(12) United States Patent
Parker

(10) Patent No.: US 8,950,742 B2
(45) Date of Patent: Feb. 10, 2015

(54) MILLING BLOCK WITH ORTHODONTIC AUXILIARY

(71) Applicant: Justin Parker, Salt Lake City, UT (US)

(72) Inventor: Justin Parker, Salt Lake City, UT (US)

(*) Notice: Subject to any disclaimer, the term of this patent is extended or adjusted under 35 U.S.C. 154(b) by 51 days.

(21) Appl. No.: 13/909,698

(22) Filed: Jun. 4, 2013

(65) Prior Publication Data

US 2014/0356798 A1  Dec. 4, 2014

(51) Int. Cl.
*B23Q 3/00* (2006.01)
*A61C 7/00* (2006.01)
*A61C 7/14* (2006.01)

(52) U.S. Cl.
CPC ............... *A61C 7/002* (2013.01); *A61C 7/146* (2013.01)
USPC .......................................... 269/287; 269/288

(58) Field of Classification Search
USPC ................................ 269/287, 288; 433/201.1
See application file for complete search history.

(56) References Cited

U.S. PATENT DOCUMENTS

| 2009/0181346 A1* | 7/2009 | Orth ........................... 433/201.1 |
| 2011/0065065 A1* | 3/2011 | Mormann ................... 433/201.1 |
| 2011/0125305 A1* | 5/2011 | Saliger et al. ................... 700/98 |

* cited by examiner

*Primary Examiner* — Lee D Wilson
*Assistant Examiner* — Shantese McDonald
(74) *Attorney, Agent, or Firm* — Marcus G. Theodore

(57) ABSTRACT

A milling block fitted with, or directly milled into said block at least one orthodontic auxiliary. These auxiliaries include but are not limited to orthodontic fasteners, buttons, cleats, tubes, brackets, springs, tad fastening clamps flex fit modules (FFM) or flex fit wafers (FFW) to be placed within the mouth and attached to teeth after custom milling of the block to conform to the anatomy of a tooth/teeth and/or TADS or other orthodontic appliances such as RPE screw and/or other orthodontic hardware.

11 Claims, 5 Drawing Sheets

MILLING BLOCK WITH ORTHODONTIC AUXILIARY

BACKGROUND OF THE INVENTION

1. Field

This invention pertains to orthodontic anchoring and appliance attachment systems. Specifically, it refers to a milling block fitted with orthodontic auxiliaries such as buttons, cleats, connecting fasteners, tubes, brackets, springs, tad fastening clamps flex fit modules (FFM) or flex fit wafers (FFW) to better position and attach these auxiliaries to the exact anatomy of the teeth within the mouth after milling to conform to the anatomy of a tooth/teeth and oral cavity.

2. State of the Art

In *Inside Dentistry*, October 2012, Volume 8, Issue 10, published by AEGIS Communications, the article entitled "Evolution of Chairside CAD/CAM Dentistry" By Masly Harsono, DMD | James F. Simon, DDS, MEd James M. Stein, DMD | Gerard Kugel, DMD, MS, PhD traces the history of computer aided manufacturing of orthodontic and dental appliances.

"The use of computer-aided manufacturing computer-aided design (CAD/CAM) systems in dentistry was introduced in the mid-1980s, and has increased dramatically during the last decade. The first generation of CAD/CAM was designed to fabricate immediate chairside inlay and onlay ceramic restorations. Initial CAD/CAM technology results looked very promising, but they required an excessive amount of time for fabrication. This first generation of computer hardware and software offered a limited 2-dimensional (2-D) view of the scanned images. The hard drive capacity was unable to store the large volume of data required for a 3-dimensional (3-D) view. The evolution of supportive computer technology over time has resulted in the chairside design and milling of complete crowns and multiple-unit ceramic restorations to a high standard. As a result, CAD/CAM scanning and milling systems have been a practical clinical reality, which makes it possible for the dental professional to produce chairside restorations.

The traditional method of making a dental impression with an elastic impression material can be alternatively performed with an intraoral digital scanner. This process is called the "optical impression." Using an optical laser or video digital technology, an intraoral digital impression-scanning wand is used to capture complete detail of the teeth and supporting soft-tissue structures. A specialized 3-D rendering program permits the images of intraorally scanned optical impressions to be visualized in 3-D on the computer monitor in real time. The dental restoration design software offered by D4D Technologies (E4D Dentist System, D4D Technologies, www.e4dsky.com) and Sirona Dental Systems (CEREC® AC, Sirona Dental Systems, www.sirona.com) is more intuitive and user friendly for the dental professional. These software programs come with features that allow dentists to mark the margins, digitally design virtual wax-up proposals of the restoration, place accurate occlusal contacts, and refine the proximal contact areas with the adjacent teeth. All of these tasks can be completed in minutes using the chairside design center before sending the final data to the computer-controlled milling unit. The following steps summarize the workflow: tooth preparation, intraoral scan, restoration design, milling of the ceramic monoblock, restoration finishing (coloring, glazing, polishing), and adhesive luting.

Simultaneously, there have occurred continual innovations in esthetic restorative materials. Monoblock ceramics can now withstand the stress of masticatory function as well as the damage introduced during the milling. The first-generation monoblocks made of feldspathic ceramic material have largely been replaced by reinforced ceramic with silica (feldspar, leucite, and lithium disilicate), non-silica (alumina and zirconia), and a combination of resin-ceramic-based materials resulting in a 3- to 11-fold increase in flexural strength. Factorial analysis of the variables influencing stress based on a computer simulation model showed that single thick monolithic all-ceramic crown materials performed better under stress compared to ceramic core material with veneering porcelain, aside from other influences. Furthermore, the coefficient of thermal expansion mismatch between core and veneer materials may initiate the internal stress that causes delaminating or internal cracking of porcelain.

The marginal fit of the milled ceramic restoration is an essential criterion for evaluating clinical success. Several investigators have evaluated the marginal fit of crown restorations fabricated with CAD systems. They reported an average marginal fit range from 25 µm to 113.88 µm. The authors' study showed that a user experienced with scanning who had completed three full training sessions produced restorations with significantly better-fitting margins than an inexperienced user who had completed a half-day training session and had no prior experience with the CAD system. Furthermore, the marginal/internal crown fit of laboratory-fabricated all-ceramic crowns showed the same accuracy as the CAD/CAM chairside systems. A marginal gap up to 120 µm is considered to be clinically acceptable with a resin-bonded luting agent, and a marginal gap up to 160 µm might be acceptable with regards to longevity although, theoretically, requirements of cementation films should be between 25 µm to 40 µm.

One concern about the ceramic block has been its monochromatic appearance. The early ceramic blocks for chairside milling were only available in limited shades. Dental professionals had to overcome this deficiency with external staining procedures. However, with the new advances in manufacturing technology, a greater selection of the blocks with esthetic qualities is available in the marketplace.

The polychromatic leucite-reinforced ceramic block (IPS Empress® Multi-block CAD, Ivoclar Vivadent, www.ivoclarvivadent.com) for E4D and CEREC systems has portioned cervical, body, and incisal segments. This block is incrementally graduated by chroma and value. This is done in an attempt to mimic the polychromatic effect of the natural dentition. The block's three ceramic segments can be portioned in the milled restoration by the design software in the restoration proposal stage.

The lithium-disilicate glass-ceramic block (IPS E.max® CAD, Ivoclar Vivadent) for the E4D and CEREC systems is now available in more values and shades, with nine high- and low-translucency blocks. Ivoclar has recently introduced its new lithium-disilicate blocks called Impulse. These blocks are available in three brightness values—V1, V2, and V3—along with two opalescent shades—Opal 1 and 2. The Opal blocks are designed mainly to create thin veneers and partial and single crowns.

The feldspar fine-particle ceramic blocks also come with two new products: Vitablocs® Triluxe Forte and Vitablocs® RealLife (Vita Zahnfabrik, www.vita-zahnfabrik.com). Currently, these two new ceramic blocks only can be used in the CEREC system. The Vitablocs Triluxe Forte contains a graded variation in color saturation—with the middle layer (body) having a regular chroma; the top layer (enamel) having a low, less intense chroma with high translucency; and the lower layer (cervical) having the highest chroma and lowest translucency. This refined color gradation provides a smoother transition of color between layers that makes it possible to match the optical characteristics of natural tooth color, including translucency and color intensity.

The Vitablocs RealLife blocks have been created to mimic the tooth's natural enamel-layered-over-dentin design. They are especially appropriate for the restoration of anterior teeth, to make them look as much as possible like natural teeth. These blocks are designed to reproduce the shade effect in regard to translucency, chroma, and lightness by positioning the restoration to be milled within the spherical dome of dentin, which is surrounded by more translucent enamel.

A reinforced resin-ceramic block has also been recently introduced to the market. The Lava™ Ultimate CAD/CAM (3M ESPE, www.3mespe.com) for the CEREC system is a unique new resin-nano-ceramic material for which the company is claiming long-lasting esthetics and performance. The advantage of this block is that post-milling oven firing is not necessary. However, data on material wear properties are not yet available at this time.

Limited clinical data using these new innovative esthetic ceramic-reinforced blocks has been reported in the literature. Herrguth et al evaluated two types of crowns made by layered-ceramic crown and monolithic CAD/CAM techniques on single anterior crown restorations. Both crowns were stained and glazed and evaluated by three independent examiners to assess the esthetic appearance. A scale of 1 to 6 was used, with 1 representing excellent characteristics and 3.5 marking the threshold of clinical acceptability. Regardless of the fabrication method, the crowns were esthetically acceptable in all 14 patients with no statistical difference between groups.

These rapid advances in ceramic monoblock technology have radically changed the performance and perceived esthetics of the restorations milled by the CAD/CAM chairside system. There are four chairside CAD systems currently available in the market for dental professionals—CEREC® AC, E4D Dentist™, Lava™ C.O.S., and the Cadent iTero™ (Cadent, www.cadentinc.com). Only two of these CAD systems, CEREC AC and E4D Dentist, have the linked CAM system unit that can mill the restorations in 7 to 30 minutes depending on the size and complexity of the restoration. The material selection to be used is decided on a case-by-case basis. For esthetic reasons, dental professionals may choose a fine feldspar-particle glass ceramic or a leucite-reinforced glass ceramic. As mentioned above, they are available in layered blocks with improved esthetic options. There are reinforced resin-ceramics, which may be chosen for their low modulus property and potential to decrease wear. These blocks do not require an additional firing process, but the leucite material does gain strength with oven firing during the stain and glaze cycles. The lithium-disilicate ceramic might be able to better withstand posterior mastication forces.

CEREC AC by Sirona is the newest version of CEREC; the earliest versions have been available since the mid-1980s. The system not only has the ability to mill a ceramic single-unit chairside restoration, but it can also mill a temporary three-unit bridge out of an acrylic block. There is also a block that functions as a wax casting (burn-out block) for a cast-metal crown. Through Sirona's digital dental network, CEREC Connect, the optical impression can be sent out digitally by e-mail to the dental laboratory for fabrication of models, multiple units, bridges, implant abutments, and zirconium or metal crowns. It can also be integrated with Sirona's Galileos system to construct surgical guides for implant placement. Sirona's CEREC Biogeneric software can analyze the individual patient's occlusion and the anatomy of the adjacent teeth so that the restoration can be designed to be patient-specific. The recently released software version, 4.0, is more intuitive and user friendly.

E4D, made by D4D Technologies, has been available since December 2007. Clinically, the system does not require the application of a contrast agent (an aerosolized spray opaque powder) on the teeth to be scanned, and the scanning wand can make contact with the target. E4D Compass integrates 3-D data from a leading cone-beam digital system that is the corollary of the Galileos system for implant surgical planning. With the release of version 2.0, E4D Dentist shares many of the above-mentioned features of the CEREC AC. The most significant shared feature is that both of these systems will be able to export their digital files in STL format, which is common to the stereolithography CAD data supported by many other 3D software packages, which are widely use in for rapid prototyping and CAM.

Based on the current information from Sirona, there are more than 11,000 CEREC users in the United States and 34,000 CEREC users internationally. This does not include the E4D systems. In addition, approximately 50 dental school in the United States use or have the CEREC or D4D CAD/CAM systems. Several dental schools have integrated the CAD/CAM technology into their pre-doctoral clinical curriculums. It has been estimated that by 2015, the number of CAD/CAM restorations—which includes crowns, bridges, veneers, and inlays—will be greater than 25% of the total units produced."

Apex Dental Milling discusses zirconia as a post-and-core material, which began in 1993 when introduced by Meyenberg et al. The technique for milling a 1-piece zirconia post and core has been described by Awad and Marghalani and Streacker and Geissberger. Computer-aided design and computer-aided manufacturing (CAD/CAM) milled zirconia posts and cores can be used when esthetic demands are important, and when the anatomy of the root canal and/or the extensive loss of the coronal tooth portion requires the use of a custom post. This technique also allows the possibility of completing a post and core in the same appointment. As stated in various reports, this technique provides a post and core with greater toughness, maximal adaptability to the canal, and adequate esthetics.

Apex Dental Milling uses the Objet Eden260V 3D printer to turn digital impressions into solid dental models for dental and orthodontic clients. The Objet 3D printing system allows small and medium sized labs to take full advantage of the revolution in digital scanning with a fully automated and accurate process that reduces their cost-per-case, allows them to achieve higher output with less manpower and ultimately, compete with larger labs.

One preferred composition for milling is Zirconia. Zirconia, which is found as zirconium dioxide, is a white crystalline oxide that exists in three phases, cubic, tetragonal, and monoclinic, depending on temperature and pressure formation. The tetragonal and monoclinic forms are used in dentistry. Zirconia in the pure tetragonal phase is unstable. In order to create the milling blocks used in our machines, dental manufacturers add yittria, creating yittria-stabilized tetragonal polycrystals (Y-TZP). In this state zirconia is extremely hard and possesses a unique characteristic called transformation toughening. When tensile stress is introduced from crack propagation, the tetragonal formation morphs into monoclinic, increasing the volume 3 to 5%, and subsequently transforms the stress from tensile to compressive. This self-healing mechanism makes zirconia the ideal material for the oral environment.

Micro crack propagation is prevented while the monoclinic transformation occurs, thereby increasing surface tension and tensile strength (i.e.,—theoretically, grinding can increase the strength of Y-TZP zirconia). But before grinding-away on your crowns, you should observe certain criteria. The severity of grinding and the rise in temperature will affect the volume percentage of toughening. They recommend using fine-grade burs and copious amounts of water coolant to decrease heat generation. Researchers have studied the quality of diamond particles impregnated in dental burs, the hardness of the binding material, and the precision and centricity of the shafts, and have found that no one manufacturer has a superior product. All manufacturers agree that hydration and very light-to-no pressure is the best technique—let the bur do the work and avoid dull tools. Also, the inside of a coping or monolithic restoration must be left untouched. It is recommended that if internal adjustments are needed for seating, the preparation should be adjusted.

A common question that arises about our TLZ all zirconia restorations concerns the wear effects they have on opposing dentition. There are many documented studies measuring the wear of zirconia against fluorapatite, porcelain, gold, lithium dicilicate, Lucite etc. These invitro studies can be summarized by focusing on particle size and finished surfaces. Zirconia is comprised of ultra-fine particles that do not become saw-tooth when roughened, unlike standard porcelains used in dental restorations. This characteristic evidently leads to low-wear of opposing enamel. A Study in J Adv Prosthodont 2010; 2:111-5 showed that wear to the antagonist teeth is much less than that of feldspathic porcelains. Moreover, the study agrees with many other studies we've reviewed, zirconia shows very low wear when highly polished.

Rella Christiansan's TRAC Research group has released preliminary results of a 7-year full-contour zirconia wear study which supports both of these claims. The study seeks to measure the amount of wear zirconia and other monolithic restorations exhibit in vivo. After one year, the "very promising" results show that zirconia "mimics" natural dentition.

As can be seen from the discussion above, the thrust of milling dentistry and orthodontics has been focused on fit, strength of materials, and color matching. There thus remains a need for a milling block fitted with integral orthodontic auxiliaries such as buttons, connecting fasteners, cleats, tubes, brackets, springs, tad fastening clamps flex fit modules (FFM) or flex fit wafers (FFW) to better position these auxiliaries within the mouth.

SUMMARY OF THE INVENTION

Orthodontics and Dento-facial Orthopedics deal in treatments often using orthodontic tooth brackets of any type integrated directly with a fastener for the purpose directing tooth movement via brackets, aligners, springs, wires, and other devices directing forces for alignment. These brackets may not fit ideally to the anatomy of the teeth due to the averages on which they are fabricated and can misalign a tooth or teeth because individuals can fall outside said averages. These issues commonly require compensatory bends and/or adjustments, repositioning, or replacement of the orthodontic appliance(s).

The present invention comprises a milling block of any material including but not limited to metal or composite, resin, ceramic or plastic block for milling, which incorporates a connected or attached orthodontic auxiliary, which would remain attached before during and after milling. Orthodontic auxiliaries as used herein comprise any orthodontic appliance or orthodontic appliance component, which assists in the activation of said appliance or assists in the connectivity of one or more orthodontic appliances or connects and/or activates parts of said orthodontic appliances or assists in activating a tooth or teeth or jaws for the purpose of moving a tooth/teeth/jaws in the service of the profession of dento-facial orthopedics and/or orthodontics.

These milled blocks with connected orthodontic auxiliaries better fit the anatomy of the tooth/teeth due to the accuracy of a digital/photo/laser scan or digital replica or virtual impression of said tooth/teeth. An exact and custom design is now possible to better position/place orthodontic auxiliaries to said teeth. This system also allows for custom design of a bracket pad of any size or shape allowing for partial or complete coverage of any surface(s) of the involved tooth. This coverage can be configured in a custom fashion to attain any amount of retentive qualities the orthodontist prefers. These optimized auxiliaries set a new standard in fit of orthodontic appliances using our or any orthodontic appliances which fit better and allow for better bonding interfaces from the orthodontic corrective appliances to the anatomy of the dentition. These auxiliaries could be but are not limited to clamps, fasteners which attaches to an appliance or a button, cleat, tube, bracket, spring, piston, sleeve, tad fastener, FFW or FFM clamps etc.

Specifically, the invention comprises a milling block of any size and or shape or any material fitted with one or more orthodontic auxiliaries (button, cleat, tube, bracket, spring, tad fastening clamp, FFW or FFM clamps etc) placed at different angles on the milling block surfaces. These milling blocks are particularly suitable for in office milling and are adaptable to accept any available holding pin required by the milling machine. The milling block with the orthodontic attachment remains on the block before during and after custom milling.

The orthodontic attachment may be an actual attachment or may simply be a second smaller block on the milling block to allow for custom milling of the attachment. The larger block can be milled to fit the tooth and to provide the proper retentive features while the other block which may or may not be smaller would be milled into a bracket or any other orthodontic auxiliary programmed into the computer for milling. The orthodontic milling block can be milled to fit a portion or all of the anatomy of any tooth and any surface of a tooth in the human dentition replacing the bracket base pad or band or crown traditionally used to attach orthodontic appliances. The auxiliary milled out of the second block can be milled into a functioning bracket, cleat, tube, fastener or any other orthodontic equipment for the purpose of tooth stabilization or movement during orthodontic treatment or stabilization before or after orthodontic treatment.

In another variation, a block in which the band/bracket or crown portion of an orthodontic appliance is milled into the block as to allow future bonding to a tooth and where the orthodontic auxiliary is milled within the same block itself with nothing attached to it before milling of the orthodontic appliance.

The invention thus provides a better fitting appliance via a superior tooth interface with an integrated auxiliary of any sort, serving a benefit to the patient with a more precise and custom orthodontic treatment in office with no impression in one visit.

DESCRIPTION OF THE ILLUSTRATED EMBODIMENT

Figure 1:
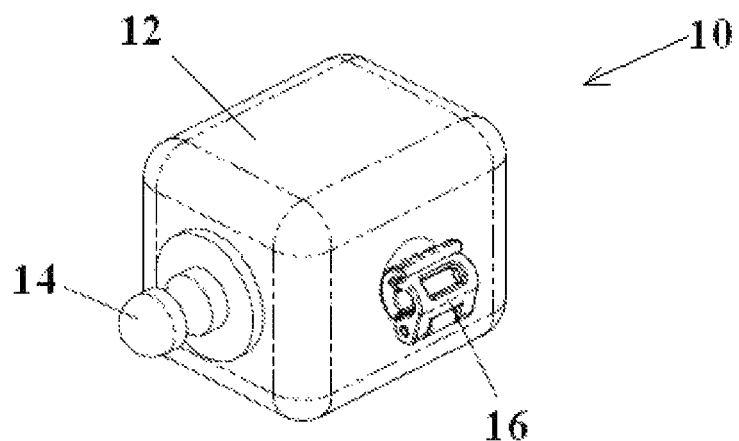
FIG. 1 is a perspective view of one embodiment of the invention with an orthodontic fastener auxiliary attached to the outside surface of the block.

FIG. 1 is a perspective view of one preferred embodiment of the invention. 10. It comprises a metal or composite/ceramic block 12 attached to a holding pin 14 to hold the block 12 for milling. Incorporated into the block 12 is a connected orthodontic auxiliary 15 shown as a clamp 16 structured to hold onto curable resin rope. The attached clamp/auxiliary 16 is present before during and after milling to insure correct positioning of the milled piece when placed in the mouth.

Figure 2:
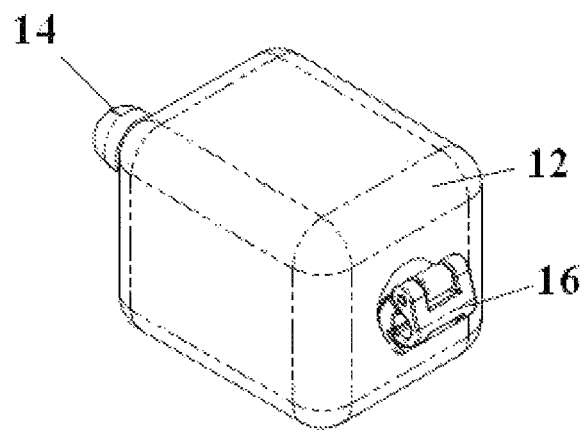
FIG. 2 is a perspective view of the embodiment of FIG. 1 with a different auxiliary fastener alignment.

FIG. 2 is a perspective view of the embodiment of FIG. 1 with a different auxiliary 15 alignment. The attachment of the clamp/auxiliary 16 constructed at a 90 degree different facing orientation to meet the needs of a patient. Although FIG. 2 and the following drawings show the auxiliaries 15 and holding pins 14 in 90 degree off-sets, these auxiliaries 15 and holding pins 14 may be positioned and manufactured in any alignment required for orthodontic treatment.

These auxiliaries 15 could be a button 17, cleat 18, tube 19, bracket 20, spring 21, tad fastening clamp 22, FFW 23, or FFM clamps 24, etc. required to be positioned against or on the tooth as part of the orthodontic treatment.

Figure 3:
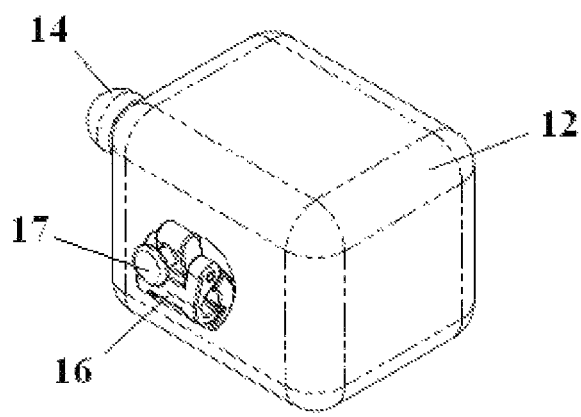
FIG. 3 is a perspective view of another embodiment of the invention with an orthodontic fastener including a button for attachment of orthodontic activation auxiliaries.

FIG. 3 is a perspective view of another preferred embodiment of the invention 10 with a metal or composite/ceramic block 12 attached to a holding pin 14 and a connected orthodontic auxiliary 15 shown as a combination clamp 16 and button 17.

Figure 4:
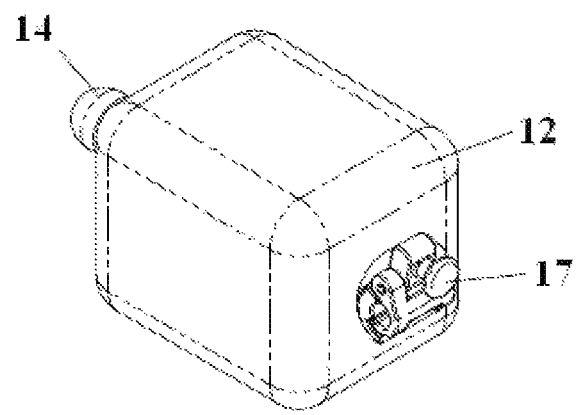
FIG. 4 is a perspective view of the embodiment of FIG. 3 with a different auxiliary alignment.

FIG. 4 is a perspective view of the embodiment of FIG. 3 with a different auxiliary 15 alignment. The combination clamp 16 and button 17 is constructed at a different facing orientation to meet the needs of a patient.

Figure 5:
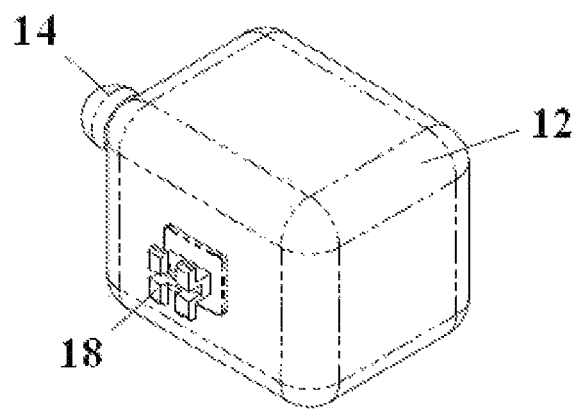
FIG. 5 is a perspective view of another embodiment of the invention with an orthodontic bracket auxiliary attached to the outside surface of the milling block.

FIG. 5 is a perspective view of another preferred embodiment of the invention with a metal or composite/ceramic block 12 attached to a holding pin 14 and connected to an orthodontic auxiliary 15 shown as a combination clamp 16, button 17, and tube 19.

Figure 6:
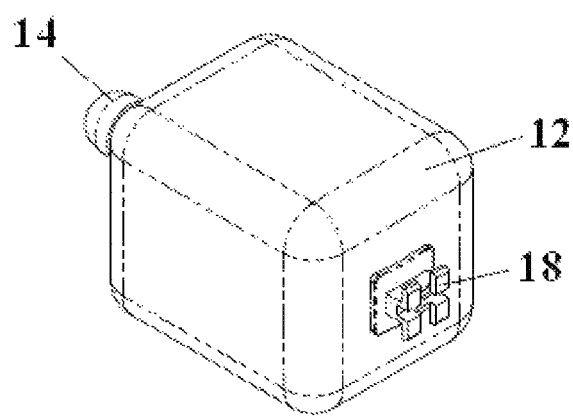
FIG. 6 is a perspective view of the embodiment of FIG. 5 with a different auxiliary alignment.

FIG. 6 is a perspective view of the embodiment of FIG. 5 with a different auxiliary alignment of the combination clamp 16, button 17, and tube 19.

Figure 7:
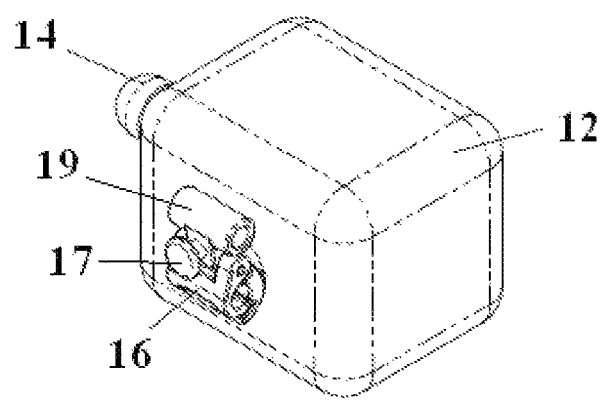
FIG. 7 is a perspective view of another embodiment of the invention including a fastener, button, and arch-wire tube auxiliaries.

FIG. 7 is a perspective view of another preferred embodiment of the invention with a metal or composite/ceramic block 12 attached to a holding pin 15 and connected to an orthodontic auxiliary 15 shown as a button 17.

Figure 8:
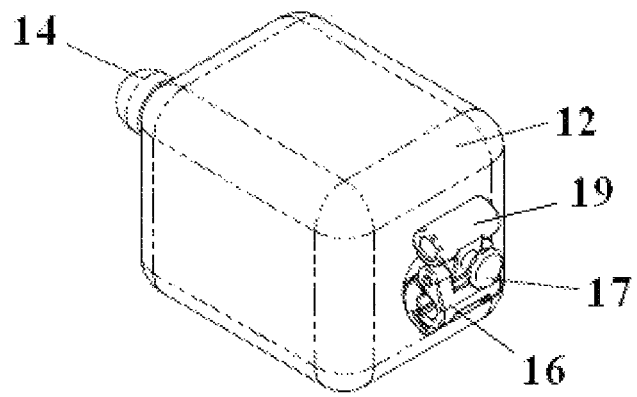
FIG. 8 is a perspective view of the embodiment of FIG. 7 with a different auxiliary alignment.

FIG. 8 is a perspective view of the embodiment of FIG. 7 with a different auxiliary 15 button 17 alignment.

Figure 9:
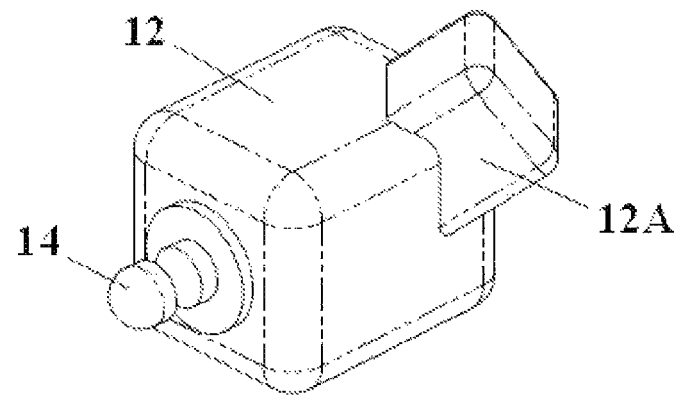
FIG. 9 is a perspective view of another embodiment of the invention with an additional milling block attached to the outside surface of the original milling block, which may be milled into any orthodontic auxiliary.

FIG. 9 is a perspective view of another preferred embodiment of the invention with a metal or composite/ceramic block 12 attached to a holding pin 14 and connected to another off-set metal or composite/ceramic block 12A.

Figure 10:
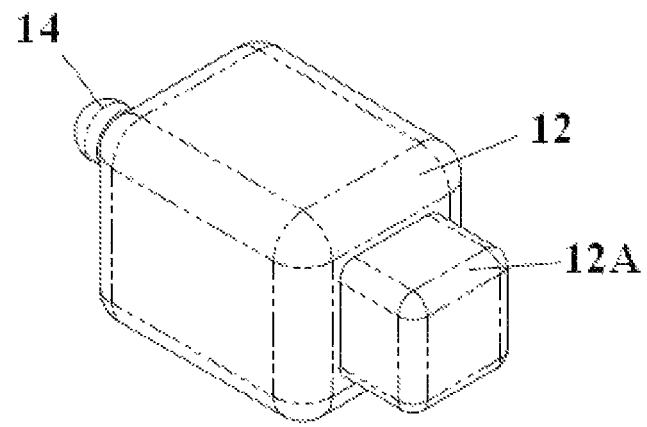
FIG. 10 is a perspective view of the embodiment of FIG. 9 with a different milling block alignment.

FIG. 10 is a perspective view of the embodiment of FIG. 9 with a different milling block 12A off-set alignment. These milling blocks 12, 12A are constructed in various alignments for milling to provide a finished orthodontic device to meet the needs of a patient.

The composition of the block 12 is selected to meet the aesthetic color preferred by a user, as well as withstand the required stresses placed on the invention 10 during orthodontic treatment or mastication. Milling is accomplished with conventional milling machines, preferably computer controlled to fit the milled block to the scanned 3D contours of the tooth or mouth.

The milled block 12 is then placed within the mouth and the auxiliaries 16 connected with wires, resin ropes, etc. to secure the tooth/teeth in place for the duration of the orthodontic treatment. This avoids the need for brackets, which may not fit the actual contours of the tooth or mouth, or misalign the angle of the auxiliary to optimize the application of vector forces. The milled block 12 is also better fitting and more comfortable to the patient.

The holding pin 14 is usually removed after milling, but may be structured as an additional connector and retained after milling to serve as an additional auxiliary to connect to other button, cleat, tube, bracket, spring, tad fastening clamp, FFW or FFM clamps etc.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:

1. A milling block to become a functional orthodontic auxiliary or appliance comprising:
    a. a block of any size and or shape or material including a milling machine holding pin so that the block may be milled to fit some or all of the contours of tooth/teeth and/or mouth and/or orthodontic appliance after said structures are scanned and milled to create an orthodontic appliance to hold or move teeth with tooth borne portions custom fabricated to connect the milled block to fit a tooth,/teeth, mouth and/or orthodontic appliance and
    b. one or more orthodontic auxiliaries (fastener, button, cleat, tube, bracket, spring, tad fastening clamp, FFW or FFM clamps) positioned onto the outside of the block for orthodontic activation after the tooth borne portions are milled leaving the orthodontic auxiliary connected as one piece to the milled custom fit tooth borne portion of appliance.

2. A milling block according to claim 1, wherein the holding pin is a dowel or attachment connected to the milling block allowing for a secure connection from the milling block to a milling machine during milling.

3. A milling block according to claim 2, wherein the holding pin is on one side of the milling block and on another side(s) is an orthodontic auxiliary, which may interconnect with other orthodontic auxiliaries after milling.

4. A milling block according to claim 1 wherein the orthodontic auxiliaries are placed and connected to the milling block on any of its surfaces including corners to allow for proper and adequate milling and post milling insertion onto a tooth or teeth in an oral cavity.

5. A milling block according to claim 1, wherein the orthodontic auxiliaries may or may not remain on the milling block before, during, and after milling.

6. A milling block according to claim 1, wherein the milling block is sized and structured to fit a portion or all of the anatomy of any tooth and any surface or combination of one or more surfaces or all surfaces of a tooth in the human dentition replacing traditional bracket base pads or bands or crowns or becoming custom milled and better fitting than traditional bracket base pads, orthodontic bands or crowns used to attach orthodontic appliances.

7. A milling block to become a functional orthodontic auxiliary or appliance comprising:
   a. a block of any size and or shape or material structured to be milled to fit some or all of contours of tooth/teeth and/or mouth and/or all or part of any orthodontic appliance after the contours are scanned before milling to create a milled custom fit tooth borne see of the milling block to hold or move teeth,
   b. one or more orthodontic auxiliaries fitted onto the milling block and positioned for optimal orthodontic activation, placement, patient comfort or ease of milling allowing tooth borne securing portions of the fastener or appliance to connect the orthodontic auxiliaries as one piece to the milled custom fit milling block, and
   c. at least one additional milling block affixed onto the primary milling block to allow for custom milling of an orthodontic attachment out of the secondary attached milling block, which the additional block(s) can be placed on any surface or multiple surfaces of the primary block including corners, transitions or surfaces as required for ease of milling and proper placement onto a tooth/teeth or appliance.

8. A milling block according to claim 7, which after the milling process, is structured for placement or attachment of the auxiliaries on any surface of any tooth in the human dentition, including distal, mesial, buccal, lingual or occlusal, or multiple surfaces or line angles of a tooth, for the purpose of moving or holding a tooth/teeth and attached to said surfaces of a tooth via tooth borne portions of a block where the anatomy of the tooth has been milled out of the original un-milled milling block(s) in any configuration.

9. A milling block according to claim 7, wherein the milling block is adapted to become the interface which allows an orthodontic appliance to be attached to a tooth via bonding of any kind to the tooth borne portions of the custom milled portions, which fit the tooth or teeth and were milled from the original orthodontic milling block or blocks in any desired configuration as ordered by the orthodontist, and which can subsequently be fastened to any orthodontic appliance or auxiliary required for tooth movement or ready to accept orthodontic forces.

10. A milling block to become an functional orthodontic auxiliary or appliance comprising:
   a. a block of any size and or shape or material structured to be milled to fit some or all of contours of tooth/teeth and/or mouth and/or all or part of any orthodontic appliance after the contours are scanned before milling to create a milled custom-fit tooth borne securing portion of the milling block to hold or move teeth,
   b. one or more orthodontic auxiliaries fitted onto the milling block and positioned for optimal orthodontic activation placement, patient comfort or ease of milling allowing tooth borne securing portions of the fastener or appliance to connect the orthodontic auxiliaries as one piece to the milled custom fit milling block, and
   c. a secondary block with an orthodontic attachment or auxiliary attached at an interface to the milling block, wherein the orthodontic attachment or auxiliary comprises any orthodontic intra-oral orthodontic instrument, device or fastener of any shape, size, material or configuration to accommodate the movement or holding of a tooth or teeth or jaws during orthodontic procedures.

11. A milling block according to claim 10, where the interface between the orthodontic attachment or auxiliary and the milling block is constructed of any kind of mechanical, chemical, structural, soldered, integral, continuous material, or adhesive interface, which can withstand the forces and environment of storage, milling, and the oral cavity including the forces place upon the after milling tooth borne portions and the post insertion orthodontic forces placed on the appliance as a unit and the auxiliary.

* * * * *